United States Patent [19]

Chikashige et al.

[11] 4,108,162
[45] Aug. 22, 1978

[54] TWISTED WIRE BRUSH WITH THREADED ASSEMBLY FOR COLLECTING CELLS

[76] Inventors: Kiyoshi Chikashige, 946-2, Otagaya, Tsurugashima-machi, Iruma-gun, Saitama; Teruo Ohuchi, No. 13-10, Kamifukuoka 4-chome, Kamifukuoka-shi, Saitama, both of Japan

[21] Appl. No.: 753,073

[22] Filed: Dec. 21, 1976

[30] Foreign Application Priority Data

Dec. 28, 1975 [JP] Japan .................. 50-158463

[51] Int. Cl.² .................................................. A61B 10/00
[52] U.S. Cl. ...................................... 128/2 B; 15/206; 128/2 W
[58] Field of Search ...... 128/2 W, 2 B, 2 M, DIG. 9, 128/304; 15/206, 164, 165

[56] References Cited

U.S. PATENT DOCUMENTS

| 1,047,021 | 12/1912 | Farnum | 15/206 |
|---|---|---|---|
| 1,669,937 | 5/1928 | Hertzberg | 15/229 AW |
| 3,613,664 | 10/1971 | Willson et al. | 128/2 B |
| 3,749,085 | 7/1973 | Willson et al. | 128/2 B |
| 3,881,464 | 5/1975 | Levene | 128/2 B |
| 3,973,556 | 8/1976 | Fleischhacker et al. | 128/2 M |

FOREIGN PATENT DOCUMENTS 137,709   4/1930   Switzerland ................ 15/206

*Primary Examiner*—Kyle L. Howell
*Attorney, Agent, or Firm*—Sughrue, Rothwell, Mion, Zinn and Macpeak

[57] ABSTRACT

A scraper brush for collecting cells from internal body passages includes a twisted wire root portion 2 mounting hairy fibers 1 between the twisted wires, and a flexible wire winding 4. A tip portion 5 of the winding 4 is stretched to present an increased pitch, and the root portion is threaded into the tip portion with the lay of the twisted wires matching the increased pitch. An additional stretched portion 5b may be provided to increase the flexibility of the brush.

7 Claims, 5 Drawing Figures

TWISTED WIRE BRUSH WITH THREADED ASSEMBLY FOR COLLECTING CELLS

BACKGROUND OF THE INVENTION

This invention relates to a brush for collecting cells for examination by brushing or rubbing a portion of a coeloma to be inspected, and more particularly to a brush which includes a flexible brush-attaching portion to allow the insertion of the brush into an area to be inspected and which allows replacement of the brush tip.

In the prior art brushes of this type as shown in FIG. 1, upon attaching a brush member in the tip portion of a flexible wire-winding, a twisted wire root portion 3 of a brush member 2 mounting hairy fibers 1 is inserted into a tip portion of a flexible wire-winding 4, and thereafter brazing is applied to the inserted portion to thereby rigidly secure the brush member 2 to the wire-winding 4. As a result, the tip portion of the flexible wire-winding 4 into which the root portion 3 is inserted loses its flexibility due to the brazing treatment. Thus, when a brush-inserting passage such as a bronchus has a sharp bend, in the course of inserting the brush up to an area to be inspected, difficulty and discomfort results which may prevent the full insertion of the brush into the bronchus, or into a deeper area. In addition, with brushes of this type the hairy fibers soon lose their ridigity, and hence premature loss of their function results. Further, with this prior art arrangement the brush member 3 cannot be removed for replacement due to the brazing, so that the entire brush has to be discarded even though other portions of the brush are free from damage.

SUMMARY OF THE INVENTION

According to the present invention, the pitch of the tip portion of the flexible wire-winding is increased so that flexibility of the wire-winding may be satisfactorily maintained, and the removal and replacement of the brush member is accomplished by merely unscrewing the brush member from the wire-winding.

DETAILED DESCRIPTION OF THE PREFERRED EMBODIMENTS

Figure 1:
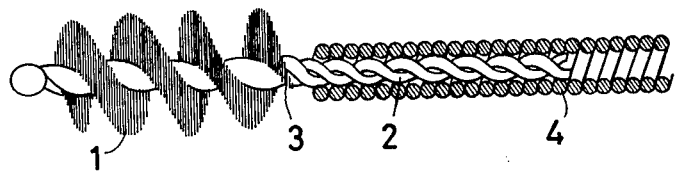
FIG. 1 shows a side view, partly in longitudinal cross section, of a prior art cell collecting brush.
Figure 2:
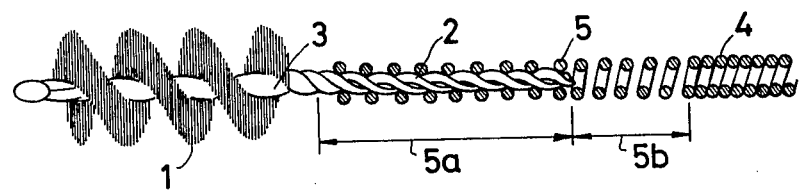
FIG. 2 shows a side view, partly in longitudinal cross section, of one embodiment of a brush according to the present invention.

FIG. 2 shows a partial longitudinal cross-sectional view of one embodiment of a brush according to the present invention. A brush member 3 consists, as is well known, of a tip portion mounting hairy fibers 1 thereon and a twisted wire root portion 2. A wire-winding 4 having a considerable length is wound around the root portion. The tip portion of the winding 4 is stretched to an increased pitch as shown at 5 relative to the lap of the two-wire twisted root portion 2. The pitch of the portion 5 substantially matches the lay of the twisted wire root portion of the brush member 3. Accordingly, the root portion 2 of the brush member 3 may be threaded into the portion 5 of the flexible wire-winding 4.

In the embodiment shown, the portion 5 consists of a portion 5a which engages the root portion 2 and a subsequent open or unoccupied portion 5b. The portion 5 may consist of only the portion 5a, however. Alternatively, the portion 5a need not be continuous with the portion 5b, but may be positioned separately or spaced therefrom. Further, the portion 5a may be made of a low hardness steel wire and roughly stretched beforehand, whereby the eventual pitch of the portion 5a may be yieldingly matched to the lay of the root portion 2 when the latter is threaded into the portion 5a.

Figure 3:
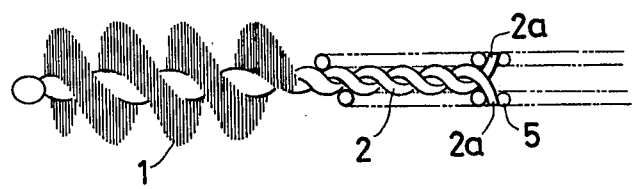
FIG. 3 shows side view of a brush member according to another embodiment of the present invention.

FIG. 3 shows a side view of the brush member of another embodiment of the present invention. The tail ends of the twisted wire root portion 2 are spread so that the legs 2a thereof may be inserted between adjoining turns of the wound portion 5 when the root portion is threaded thereinto.

Figure 4:
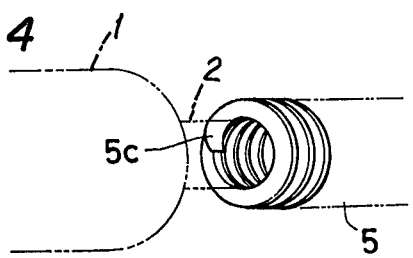
FIG. 4 shows a perspective view of one end of a flexible wire-winding.

FIG. 4 shows a perspective view of a brush attaching end of the flexible wire-winding in still another embodiment of the present invention. In this embodiment an end 5c of the wound portion 5 of the wire-winding 4 is bent radially internally to some extent, thereby bearing against the root portion 2 of the brush member as it is threaded into the portion 5 and serving to better engage the lay thereof in the manner of an additional thread.

Figure 5:
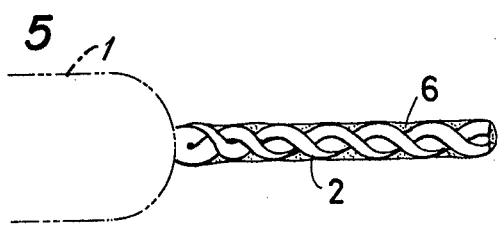
FIG. 5 shows a side view of the brush of yet another embodiment of present invention.

FIG. 5 is a side view of the twisted wire root portion of a yet another embodiment of the present invention. A thin coating 6 of plastic or solder is formed on the root portion 2 to provide a close fit between the root portion and the wound portion 5 when the former is threaded into the latter. Alternatively, a soft plastic may be coated on the inner surface of the wound portion 5 to similarly provide a closer and more positive fit during and after insertion. In addition, a stop may be provided on the root portion 2 at the rear of the hairy fibers to limit the length of the root portion which may be threaded into the wound portion 5, to thereby ensure a uniform and proper position after assembly.

The elongated flexible wire-winding may be stretched to provide the portion 5 of increased pitch, or the portion 5 may be formed separately and then welded to one end of the flexible wire-winding 4. Thereafter, the twisted wire root portion is threaded into tight engagement with the wound portion 5 by hand or with special tool. Since the lap of the root portion is matched to the pitch of the wound portion the threaded engagement effectively prevents the brush member 3 from coming off during use.

When the brush member 3 becomes worn during service, it is merely unscrewed or unthreaded from the wound portion 5, whereby replacement may be easily accomplished. Since the brush member engages the wound portion of the flexible wire-winding 4 without the use of brazing or the like, the flexibility of the engaging portion is not impaired. In addition, when another wound portion 5b is provided after the engaging portion 5a, further flexibility may be attained to the extent that the operation of the brush will not be adversely affected. As a result, the brush according to this invention may be inserted into a curved body vessel along the mucous membrane thereof, and the brush may also be used for cleaning the inner wall of a bent vessel or passage.

What is claimed is:

1. A brush for collecting cells for examination, comprising; a twisted wire root portion having hairy materials extending radially outwardly from an end portion thereof, said materials being held between two twisted wires of said root portion; and an elongated flexible wire winding having a tip portion threadingly engaging said twisted wire root portion, the pitch of said tip portion being greater than the pitch of a remaining portion of said winding such that the lay of said wire root portion matches the pitch of said tip portion.

2. A brush as defined in claim 1, wherein the length of said tip portion is greater than the depth to which said root portion is inserted.

3. A brush as defined in claim 1, wherein said flexible wire winding includes a further portion separated from said tip portion by said remaining portion, said further portion having a pitch which is greater than the pitch of said remaining portion.

4. A brush as defined in claim 1, wherein the ends of the two twisted wires of said root portion extend radially outwardly between adjacent wire turns of said tip portion.

5. A brush as defined in claim 1, wherein the end of said flexible wire winding is bent radially inwardly to threadingly engage the lay of said twisted wire root portion.

6. A brush as defined in claim 1, wherein said twisted wire root portion is coated with plastic material.

7. A brush as defined in claim 1, wherein said twisted wire root portion is coated with solder.

* * * * *